United States Patent [19]

Crawford et al.

[11] 4,058,131

[45] Nov. 15, 1977

[54] IMPROVING HAIR BODY AND MANAGEABILITY WITH DIPERISOPHTHALIC ACID

[75] Inventors: Richard J. Crawford, Highland Park; Clarence R. Robbins, Piscataway, both of N.J.

[73] Assignee: Colgate-Palmolive Company, New York, N.Y.

[21] Appl. No.: 666,378

[22] Filed: Mar. 11, 1976

Related U.S. Application Data

[63] Continuation of Ser. No. 506,462, Sept. 16, 1974, abandoned, which is a continuation of Ser. No. 219,510, Jan. 20, 1972, abandoned.

[51] Int. Cl.$^2$ .......................... A45D 7/04; A61K 7/06
[52] U.S. Cl. ............................. 132/7; 8/111; 252/186; 424/DIG. 3; 424/62; 424/70
[58] Field of Search ...................... 424/70, 62, DIG. 3; 132/7; 252/1, 86; 8/111

[56] References Cited

U.S. PATENT DOCUMENTS

| | | | |
|---|---|---|---|
| 1,547,187 | 7/1925 | Weiss | 252/186 |
| 2,347,434 | 4/1944 | Reichert et al. | 260/502 |
| 3,075,921 | 1/1963 | Brocklehurst et al. | 252/99 |
| 3,248,336 | 4/1966 | Blumbergs | 252/186 |
| 3,365,487 | 1/1968 | Gonse | 260/502 |
| 3,384,596 | 5/1968 | Moyer | 252/187 |
| 3,472,604 | 10/1969 | Dasher et al. | 8/10.2 |
| 3,633,591 | 1/1972 | Anzuino et al. | 132/7 |
| 3,639,285 | 2/1972 | Nielsen | 252/186 X |

*Primary Examiner*—Albert T. Meyers
*Assistant Examiner*—Vera C. Clarke
*Attorney, Agent, or Firm*—Herbert S. Sylvester; Murray M. Grill; Norman Blumenkopf

[57] ABSTRACT

A method and composition for improving hair body and manageability while not effecting a change in color, such method comprising applying to the hair an effective amount of an aqueous solution of from about 0.1% to about 10% by weight of an aromatic peracid oxidizing agent, particularly m-chloroperbenzoic acid and diperisophthalic acid, the aromatic peracid oxidizing agents providing maximum reaction with the fiber surface producing increased hair body and manageability with minimum diffusion into the interior of the hair so as to avoid effecting a change in color.

5 Claims, No Drawings

IMPROVING HAIR BODY AND MANAGEABILITY WITH DIPERISOPHTHALIC ACID

This is a continuation, of application Ser. No. 506,462 filed Sept. 16, 1974 now abandoned, which is a continuation application of Ser. No. 219,510, filed Jan. 20, 1972, now abandoned.

This invention relates to a method and composition for improving hair body and manageability while not changing the color of the hair. More particularly, this invention relates to a method and composition for improving hair body and manageability by treating the fiber surface with an oxidizing agent which reacts primarily on the surface of the hair with little or no diffusion into the interior of the hair fiber.

Friction and other surface characteristics influence the composition of the hair such as combability and conditioning or overall manageability. While hair-on-hair friction and hair-on-other-surface friction is not always desirable, since this makes wet combing of the hair a difficult operation, these frictional effects, especially hair-on-hair friction, are important with respect to the manageability and body of hair. More particularly, these frictional effects are related directly to the ability of hair to maintain a set or coiffure for a substantial period of time. These frictional effects and some factors influencing the same are set forth in an article published in the Journal of the Society of Cosmetic Chemists, Vol. XIV, No. 9, p. 455, Sept., 1963. In this article, the authors recognize that chemical bleaching utilizing peroxides and ammonia almost doubles the hair-on-hair frictional characteristics of the hair. Furthermore, U.S. Pat. No. 3,577,528 recognizes that hair which has been chemically bleached or bleached by the effect of sunlight is especially difficult to comb in the wet state. However, if these bleached hairs are treated with so-called cream rinse products, the hair becomes limp and soft and is not able to maintain a set or coiffure. Both of the above-noted references recognize the effects of bleaching of hair on the frictional effects of hair-on-hair and the effect of these frictional effects on the manageability or ability of the hair to hold a set.

Although it has been recognized that bleaching affects the hair and improves the manageability of the same with regard to maintaining a set, no products or methods for treating the hair are available which utilize the inherent increase in frictional properties of the hair by treating with an oxidizing agent, while at the same time not substantially affecting the color of the hair in any manner. The above-noted prior art methods of increasing the frictional effects of the hair and thereby affecting manageability and holding properties also bleached or lightened the color of the hair, i.e., by the use of a conventional peroxide-ammonium hydroxide, or photo-oxidation bleaching process.

Prior art attempts to produce which would improve the body and manageability of the hair without bleaching or oxidizing the hair so as to change the color of the same have not been completely successful since resins which promote the body and manageability of hair are removed by shampooing and must be replenished or reapplied to the hair after each shampoo.

It has been found, however, that by utilizing the process and composition of the present invention, a permanent improvement in body and manageability of the hair may be obtained without any significant change in the color thereof. Briefly, the method of the present invention comprises applying to the hair an effective amount of an aqueous solution of from about 0.1 to about 10% by weight of an aromatic peracid oxidizing agent, particularly m-chloroperbenzoic acid and diperisophthalic acid, the aromatic peracid oxidizing agent providing maximum reaction with the fiber surface of the hair, thereby imparting increased hair body and manageability with a minimum of diffusion into the interior of the hair so as to substantially avoid a color change. The composition of the present invention comprises an aqueous solution of from about 1 to about 10% by weight of the above-noted aromatic peracid oxidizing agent.

Accordingly, it is the primary object of the present invention to provide a composition for "permanently" improving the manageability and body of hair, while not effecting a color change.

It is a further object of the present invention to provide a method for improving hair body and manageability without changing the color of the same by applying an effective amount of an oxidizing agent which reacts only with the surface of the hair and does not diffuse into the interior of the same so as to affect the color.

It is a still further object of the present invention to provide a composition comprising an aqueous solution of from about 1 to about 10% by weight of an aromatic peracid oxidizing agent.

It is a still further object of the present invention to provide a method for improving hair body and manageability without substantially changing the color of the same by applying an aqueous solution comprising an effective amount of an aromatic peracid oxidizing agent.

Still further objects and advantages of the method and composition of the present invention will become more apparent from the following more detailed description thereof.

The method of the present invention comprises applying to the hair an effective amount of an aqueous solution of from about 0.1 to about 10% by weight of aromatic peracid oxidizing agent, the solution having a pH of from 8 to 11, for a period of time up to about one hour.

The composition of the present invention comprises an aqueous solution of from about 0.1 to about 10% by weight of an aromatic peracid oxidizing agent, the solution having a pH of from 8 to 11.

Although not wishing to be limited to any specific theory or mechanism as to why the composition and method of the present invention effectively improves the body and manageability of the hair, while minimizing any color change, the following appears to describe and explain this occurance. The oxidizing agents utilized in the composition and method of the present invention are aromatic peracid oxidizing agents, these compounds being sufficiently large so that it appears that the major effect of these oxidizing agents is on the surface of the hair fibers themselves, with a minimum of diffusion of the oxidizing agents into the interior of the hair where the pigment or color of the hair resides. By reacting only on the surface of the hair fibers, and not reacting with the center pigment portion of the hair, the desirable frictional properties imparted by oxidizing treatments of the hair are obtained without a substantial change in the color of the hair fibers themselves.

Suitable aromatic peracids for use in the method and composition of the present invention include the following compounds: m-chloroperbenzoic acid, diperisophthalic acid, perbenzoic acid, perphthalic acid, etc. Although any of the above-noted aromatic peracid compounds may be utilized in the composition and method of the present invention m-chloroperbenzoic acid and diperisophthalic acid are preferred.

The composition of the present invention comprises an aqueous solution of the above-noted aromatic peracid oxidizing agents at a concentration of from about 0.1 to about 10% by weight. Within this concentration range, the oxidizing activity of the peracid compounds appears to be primarily limited to affecting the surfaces of the hair fibers with little or no diffusion of the oxidizing agents into the interior of the hair wherein the pigment of the hair fibers resides. Within the above-noted range, however, it has been found that solutions having a concentration of from 1 to 6% oxidizing agents are preferred. It is within this preferred range that a maximum roughening effect of the hair with the increase in manageability and body occurs with a minimizing of the possibility of breakdown of the aromatic peracids into hydrogen peroxide, which could effect a color change in the hair.

The treatment time in accordance with the method of the present invention may vary somewhat, depending upon the desired effect. In other words, if the hair to be treated has some natural body and manageability, the treatment time will not have to be as long as that for hair which is completely limp and unmanageable. In general, it has been found that treatment times of up to about 1 hour impart the desired effect of an increase in manageability by roughening the fiber surfaces with a minimum of diffusion into the center of the hair causing a color change. Although the treatment time may vary in accordance with the concentration of aromatic peracid oxidizing agent utilized, i.e., the more concentrated the solution, the shorter the treatment time necessary, within the above-noted preferred concentration range, it has been found that optimum effects have been obtained utilizing a treatment time within the range of from about 15 to 40 minutes. Again, the treatment times will vary in accordance with a great number of other parameters, namely, the treatment history of the hair to be treated and the general character and texture of the individual's hair.

A third parameter which again will vary markedly depending upon the individual to be treated, and the treatment history of the hair, and other natural characteristics of the hair, is the solution-to-hair ratio. Generally, it has been found that a solution-to-hair ratio of from about 25:1 to about 1:1 by weight produces satisfactory results. Within the above-noted weight ratio, it has generally been found that a solution-to-hair ratio of from about 10:1 to about 1:1 produces optimum results.

The temperature at which the composition of the present invention is applied to the hair is not particularly important since the method of treating the hair is not particularly dependent on temperature. However, high drying temperatures should be avoided immediately after treatment with the aromatic peracid solutions and before complete rinsing since these high temperatures tend to decompose the peracids into hydrogen peroxide which can affect the color of the hair. For this manner, it is preferable that, if the hair is to be dried and set subsequent to treatment with the composition of the present invention, the hair should be thoroughly rinsed to remove the peracid so that the drying or other heat treatments will not cause decomposition to hydrogen peroxide. Again, although it is preferred to apply the composition of the present invention to hair which has been first shampooed, this initial cleaning treatment is not necessary for the successful improvement of hair body and manageability according to the method of the present invention.

The oxidizing treatment for improving hair manageability and body may be carried out either in a single treatment utilizing a high solution-to-hair ratio or may be carried out in a series of successive treatments utilizing a low solution-to-hair ratio. Either of the above-noted methods produces satisfactory results. Since the treatment is dependent upon a large number of parameters, the characteristics of the individual's hair to be treated must be first determined before deciding on a single concentrated treatment or a series of less concentrated treatments. In either case, the end result is substantially the same whether a single treatment is utilized or a series of treatments are utilized.

The composition and method of the present invention will now be illustrated by the following examples, which are in no way to be considered limiting, wherein all parts, percentages and ratios are by weight, and all temperatures in degrees Centigrade.

EXAMPLES 1-7

Tresses of hair are shampooed, rinsed with water and dried. The tresses are then treated with the following aqueous solutions of diperisophthalic acid, as in Table I, adjusted to pH 10 with ammonium hydroxide in a solution-to-hair ratio of 25:1 for 30 minutes. Subsequent to this treatment, the tresses are rinsed with water, and set and dried.

Table I

| Example | Concentration (wt. %) |
| --- | --- |
| 1 | 1.0 |
| 2 | 1.0 |
| 3 | 2.0 |
| 4 | 3.0 |
| 5 | 4.0 |
| 6 | 5.0 |
| 7 | 10.0 |

Each of the above tresses has improved body and manageability as shown by combing and curl retention with substantially no color change.

EXAMPLES 8-14

Examples 1-7 are repeated except that the hair is treated with aqueous solutions of m-chloroperbenzoic acid. Each of the tresses so treated shows improvement in body and manageability.

EXAMPLES 15-21

Examples 1-7 are repeated except that the tresses are treated three times with a solution-to-hair ratio of 2.5:1. After the first treatment, some improvement is noted, while after the second and third treatments, substantially the same improvement as in Examples 1-7 is noted.

EXAMPLES 22-28

Examples 15-21 are repeated except that solutions of m-chloroperbenzoic acid are used with similar results.

EXAMPLES 29-30

All of the foregoing examples are repeated, substituting solutions of perbenzoic acid and perphthalic acid, with similar results.

Some of the peracids used in this invention may be difficult to handle safely in 100% active form, particularly diperisophthalic acid, and consequently it is preferred to formulate solutions therefrom using diluted or encapsulated forms of the percompound. An example of this is a composition comprising diperisophthalic acid (25%) encapsulated with magnesium sulfate (75%).

While the process and composition of the present invention have been illustrated by way of foregoing examples and specifications, the present invention is to be in no way limited thereto, but should be limited only as defined in the following claims.

What is claimed is:

1. A method of improving the manageability and body of hair which comprises treating the hair with an effective amount of an aqueous solution having a pH of 8 to 11 and containing about 0.1 to about 10% by weight of diperisophthalic acid for a treatment time, up to one hour, sufficient to improve the manageability and body of the hair while not effecting a change in the color thereof.

2. A method according to claim 1 wherein the aqueous solution is applied to the hair in a ratio of aqueous solution to hair of about 1:1 to 25:1, and the application time is 15 to 40 minutes.

3. A method of improving the manageability and body of hair according to claim 1 wherein the hair is human hair.

4. A method according to claim 2 wherein the aqueous solution is at a concentration of about 1 to 6% of said acid agent, and further including the steps of thoroughly rinsing the solution from the hair, setting the hair and drying the hair.

5. A method according to claim 4 wherein the hair is so treated three times, and in each treatment a solution: hair ratio of about 2.5:1 is employed, so that after the third treatment substantial improvement in body and manageability of the hair results.

* * * * *